United States Patent [19]

Sato et al.

[11] Patent Number: 4,561,429
[45] Date of Patent: Dec. 31, 1985

[54] FLASHLIGHT CONTROL APPARATUS FOR ENDOSCOPE

[75] Inventors: Ken Sato; Yutaka Takahashi; Takashi Tsukaya; Shinichi Kato; Shinichiro Hattori, all of Tokyo, Japan

[73] Assignee: Olympus Optical Co., Ltd., Tokyo, Japan

[21] Appl. No.: 540,837

[22] Filed: Oct. 11, 1983

[30] Foreign Application Priority Data

Oct. 15, 1982 [JP] Japan ................... 57-180846

[51] Int. Cl.⁴ .............................................. A61B 1/06
[52] U.S. Cl. ............................................ 128/6; 354/62
[58] Field of Search ................... 128/6, 4; 350/96, 26; 354/62

[56] References Cited

U.S. PATENT DOCUMENTS

| Re. 31,289 | 6/1983 | Moore et al. | 128/6 |
|---|---|---|---|
| Re. 31,290 | 6/1983 | Moore et al. | 128/6 |
| 3,599,630 | 8/1971 | Sato et al. | 128/6 |
| 4,053,756 | 10/1977 | Takahashi | 128/6 X |
| 4,074,306 | 2/1978 | Kakinuma et al. | 128/6 X |
| 4,253,447 | 3/1981 | Moore et al. | 128/6 |
| 4,261,344 | 4/1981 | Moore et al. | 128/6 |
| 4,310,228 | 1/1982 | Terada | 128/6 X |
| 4,349,014 | 9/1982 | Takamatsu | 128/6 |
| 4,384,775 | 5/1983 | Hosoda | 128/6 X |
| 4,416,524 | 11/1983 | Takayama | 128/6 X |
| 4,429,686 | 2/1984 | Hosoda | 128/6 |
| 4,524,761 | 6/1985 | Hattori et al. | 128/6 |
| 4,527,552 | 7/1985 | Hattori | 128/6 |

Primary Examiner—William H. Grieb
Attorney, Agent, or Firm—Frishauf, Holtz, Goodman & Woodward

[57] ABSTRACT

A light flash control apparatus is used for an endoscope in which a solid-state image sensor is employed. A image signal derived from the solid-state image sensor during the illumination by a halogen lamp is also utilized as a photo-metric signal. An adequate quantity of flashlight for the image sensor is calculated in advance based upon the photo-metric signal. The calculated exposure time i.e., the desirable quantity of flashlight is stored in an integration circuit. After the given exposure time passes since the flash tube is ignited, it is forcibly turned-off by a turn-off thyristor.

4 Claims, 5 Drawing Figures

FLASHLIGHT CONTROL APPARATUS FOR ENDOSCOPE

BACKGROUND OF THE INVENTION

This invention generally relates to a flashlight control apparatus for an endoscope, and more particularly, to a flashlight control apparatus for an endoscope in which a solid-state image sensor is employed and an exposure time required for high-speed flash photography is pre-calculated based upon a received photo-metric signal from the solid-state image sensor.

The development of the solid-state image sensor has opened the door to substantial progress in the state of the art of high resolution, compactness and small power consumption.

It is generally desirable to automatically control an exposure time of the flashlight by means of an automatic exposure control device when photographing diseased portions in a patent, by utilizing an endoscope. In the automatic exposure control device of the type mentioned, an automatic exposure control operation is effected in such a manner that when an exposure of light reflected from the diseased portions (foreground subject) becomes a predetermined level, the flashlight is forcibly interrupted by an electronics means.

In the case when the known automatic exposure device is employed in the endoscope, there are provided various disadvantages in that a complex optical system, e.g., a beam splitter is necessarily required, resulting in a bulky in size and expensive cost.

A primary object of the present invention is to realize automatic exposure photography, by use of a flashlight, with an endoscope in which a solid-state image sensor is assembled.

A secondary object of the present invention is to realize high-speed flashlight photography for diseased portions, e.g. a stomach, the motion of which is rapidly changed, with an endoscope in which a solid-state image sensor is assembled.

A third object of the present invention is to provide a flashlight control apparatus for an endoscope in which a solid-state image sensor is employed as a photo-metric optical element as well as a photographing element, so that the camera unit employing the solid-state image sensor becomes compact.

A fourth object of the present invention is to provide a flashlight control apparatus for an endoscope in which a solid-state image sensor is employed so that precise optical adjustment e.g. an alignment of the photo-metric optical system is avoided.

SUMMARY OF THE INVENTION

The objects of the present invention may be accomplished by providing a flashlight control apparatus for an endoscope comprising:

light source means which is coupled to one end of a light guide member of an endoscope body and at least includes a lamp for monitor purposes, a flash tube for photographic purposes, and a light path selecting member which is arranged in such a manner that two lights from said lamp and flash tube are selectively transferred via said light guide member to a foreground subject;

camera means which is detachably mounted to said endoscope body and at least includes a solid-state image sensor optically coupled to an image guide member of said endoscope body;

a flashlight control circuit which is connected to said flash tube and includes a turn-on/turn-off control circuit and a programmed exposure/light processing circuit; and camera control means which is electrically connected to said solid-state image sensor so as to receive image signals of the foreground subject and connected to said flashlight control circuit so as to apply photo-metric signals, wherein said photo-metric signals are derived from said image signals while said foreground subject is illuminated by said lamp for monitor purposes, said photo-metric signal is calculated in said exposure/light processing circuit so as to obtain an exposure value desirable for photographic purposes, and turning-on/turning-off of said flash tube is controlled based upon said desirable exposure value.

Furthermore it may be also accomplished by providing a flashlight control apparatus for an endoscope comprising:

light source means which is coupled to one end of a light guide member of an endoscope body and at least includes a lamp for monitor purposes, a flash tube for photographic purposes, and a light path selecting member which is arranged in such a manner that two lights from said lamp and flash tube are selectively transferred via said light guide member to a foreground subject;

camera means which is mounted to a distal end of said endoscope body located near an opposite end of said light guide member, and at least includes a solid-state image sensor which may receive optical images of said foreground subject;

a flashlight control circuit which is connected to said flash tube and includes a turn-on/turn-off control circuit and an exposure/light processing circuit; and camera control means which is electrically connected via a signal transfer member to said solid-state image sensor so as to receive image signals of the foreground subject and connected to said flashlight control circuit so as to apply photo-metric signals, wherein said photo-metric signals are derived from said image signals while said foreground subject is illuminated by said lamp for monitor purposes, said photo-metric signal is calculated in said exposure/light processing circuit so as to obtain an exposure value desirable for photographic purposes, and turningon/turning-off of said flash tube is controlled based upon said desirable exposure value.

BRIEF DESCRIPTION OF THE DRAWINGS

The invention may be best understood with reference to accompanying drawings, in which.

DETAILED DESCRIPTION OF THE PREFERRED EMBODIMENTS

Before proceeding with the various types of preferred embodiments, the fundamental operation of a conventional endoscope will now be summarized.

Figure 1:
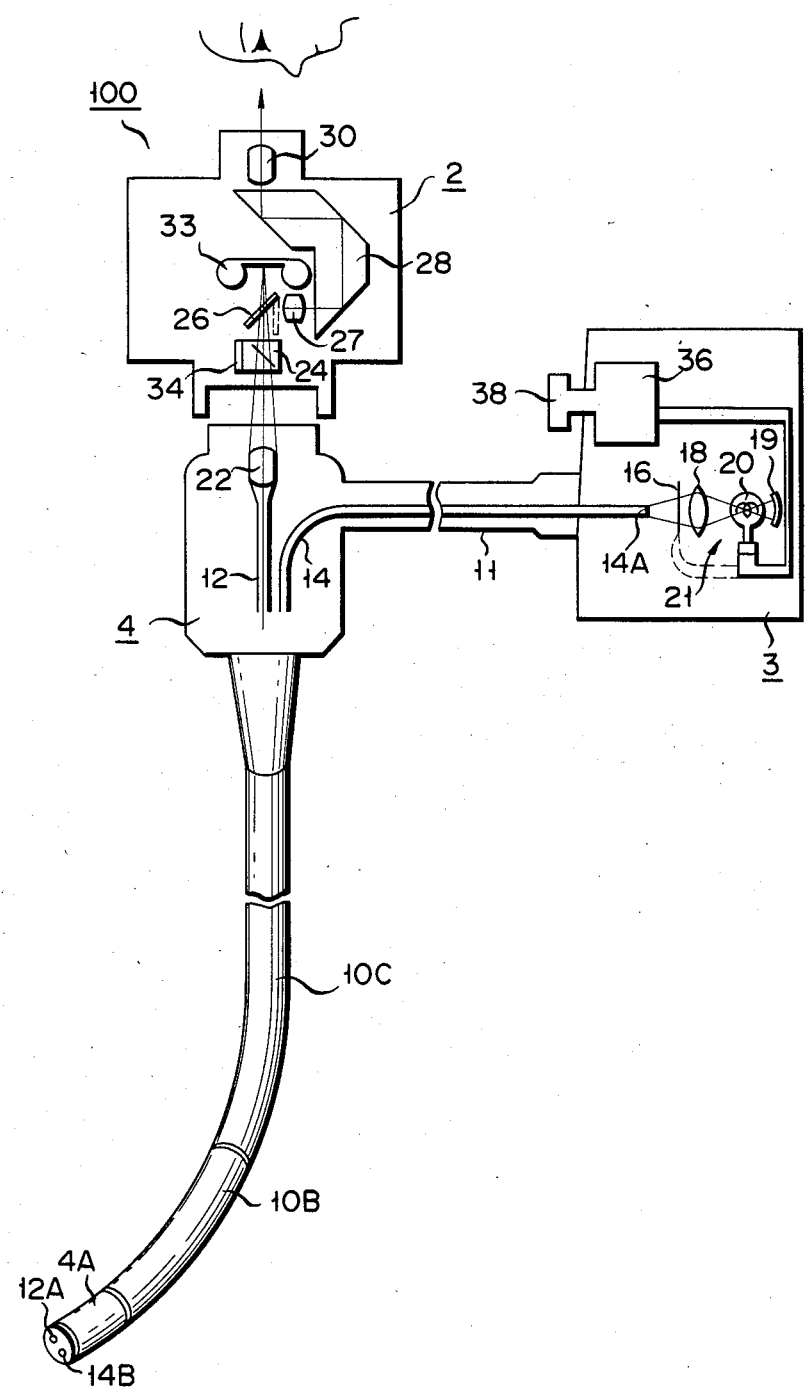
FIG. 1 is a schematic representation of a conventional endoscope.

FIG. 1 is a schematic representation of the conventional endoscope. The endoscope 100 is mainly comprised of an endoscope body 4, a camera unit 2, and a light source unit 3.

The endoscope body 4 has a fiber image guide 12 for transferring optical images of the diseased portions and a fiber light guide 14. Light from a lamp 20 is coupled through a condenser lens 18 and a diaphragm 16 to a light receiving end 14A of the fiber light guide 14. A reflector 19 is disposed on the back of the lamp 20 to increase the illumination efficiency. The diaphragm 16 and lamp 20 constitute a light source section 21. Light coupled to the light receiving end 14A of the fiber light guide 14 is led therethrough and emitted from a light guide end 14B of a distal end 4A. The distal end 4A is connected through a bendable section 10B and a flexible tube (insertion tube) 10C to the endoscope body 4. The distal end 4A has a conventional observational optical system 12A provided within it. An optical image of diseased portions caught by the optical system 12A is led through the fiber image guide 12 to a lens system 22. The optical image having been transmitted through the lens system 22 is transmitted through a semi-transparent prism 24 and led to a movable mirror 26. When photographing is not made, the optical image incident on the movable mirror 26 is led through a lens system 27, a penta-prism 28 and a lens system 30 to the outside of the camera unit 2 which is to be mounted on the endoscope body 4. On the other hand, when taking a picture, the movable mirror 26 is moved to a position shown in broken lines in FIG. 1. As a result, the optical image having been transmitted through the semi-transparent prism 24 is led to a film 33.

The aforementioned optical image is spectroscopically split by the semi-transparent prism 24, and part of it is led therefrom to the left in FIG. 1. The prism 24 is provided at its left hand end with a photoelectric converter or photo-diode 34. The photoelectric converter may be a cadmium sulfide (CdS) cell or a solar battery. The photo-diode 34 produces a brightness signal at a level corresponding to the brightness of the optical image transmitted through the prism 24.

This brightness signal is generally used for determining an adequate exposure for photography (and will be explained in detail hereinafter).

A light source control device 36 is provided in the light source unit 3 and connected to the lamp 20 so as to control the quantity of light given by the light source section 21 to the light receiving end 14B of the fiber light guide 14 by adjusting a control knob 38. The light source unit 3 is constituted by the light source 21 and the light source control device 36. The light source unit 3 is mounted on the endoscope body 4 via a light guide protective tube 11.

The photographing apparatus shown in FIG. 1 is used in the following way. When taking a picture after mounting the camera 2 on the endoscope body 4, the eyepiece (not shown) of the endoscope is removed from the optical path. The movable mirror 26 is set at its position of solid lines in FIG. 1 until a spot to be photographed is found out. When the photographing spot is determined, a shutter release switch (not shown) is depressed. It should be noted that the lamp 20 has two functions, one for illuminating the diseased portions during the observation of the photographing spot, and the other for applying a light flash to them by controlling the diaphragm 16.

With the operation of the shutter release switch, the movable mirror 26 is moved to its position of broken lines in the FIG. 1. Then, the lamp 20 is caused to flash. The flashlight is reflected by the aforementioned photographing spot ahead of the distal end 4A, and the optical image of the spot is led through the semi-transparent prism 24 to the film 33. The brightness of the optical image at this time is detected by the photo-diode 34. When an adequate quantity of exposure light is obtained, the illumination by the lamp 20 is interrupted. During the "off" period of the lamp, the movable mirror 26 is returned to the position of solid lines in the Figure, and then the illumination by the lamp 20 is resumed. In this way, one photographing cycle or sequence is ended. The adequate exposure light quantity is suitably determined in dependence upon the sensitivity of the film 33 used, and other conditions.

Figure 2:
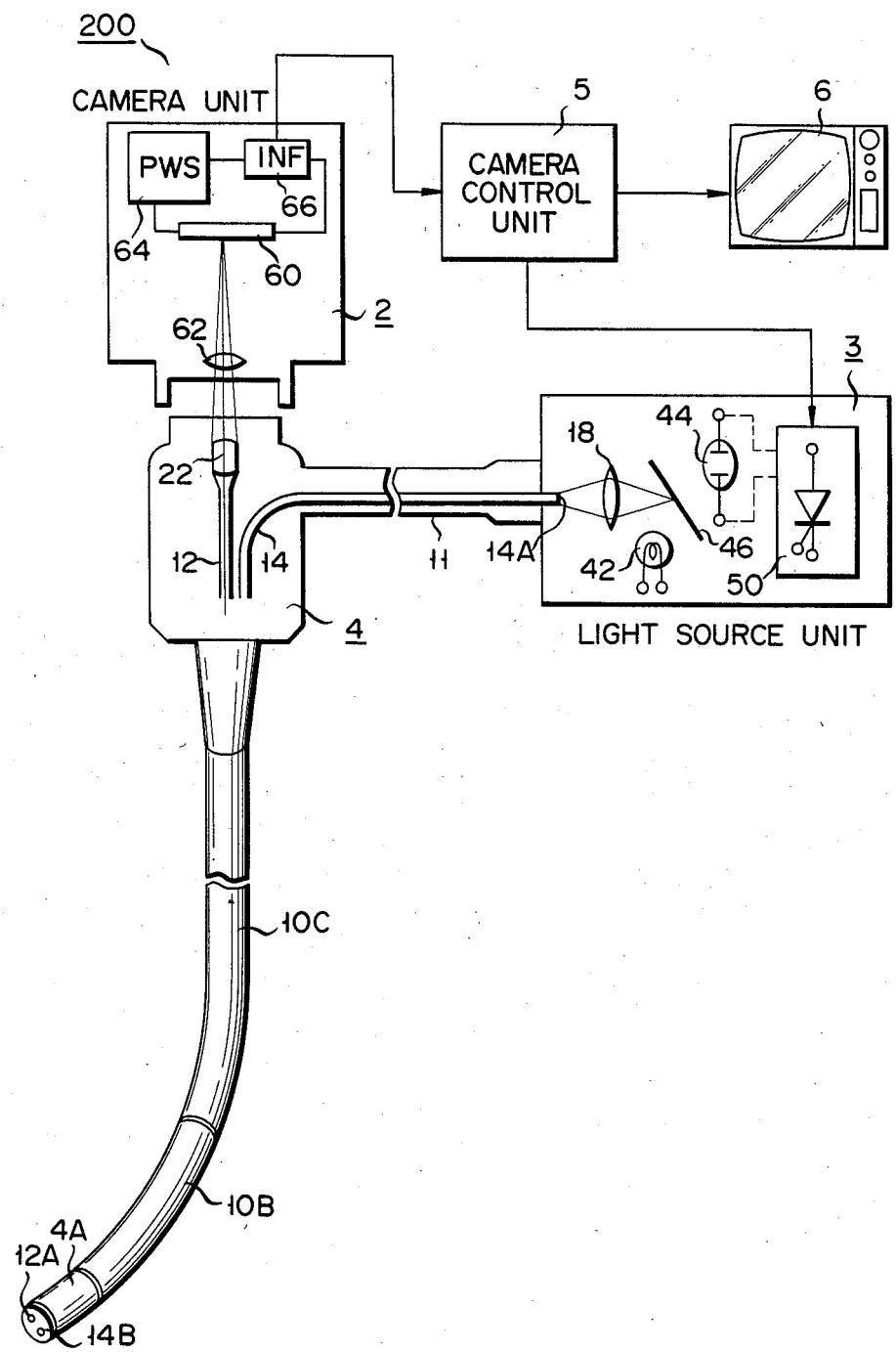
FIG. 2 is a schematic representation of a flashlight control apparatus combined with an endoscope according to one preferred embodiment of the present invention.

Referring to FIG. 2, one preferred embodiment is disclosed in which a flashlight control apparatus is employed in an endoscope 200. It should be noted that the same reference numerals shown in FIG. 1 will be employed as those for denoting the same circuit elements shown in the following figures.

The endoscope 200 is mainly constituted by an endoscope body 4, a camera unit 2, a light source unit 3 and a camera control unit 5, and a monitor 6 is connected to the camera control unit 5 for monitoring images of a foreground subject.

A description will be first given to the light source unit 3. In the light source unit 3, a halogen lamp 42 and a flash tube 44 of a flashlight control circuit 50 are arranged to face with a fiber light guide 14 through a movable mirror 46. Halogen light (=light for monitor purposes) and flashlight (=light for photography purposes) may be selected for illumination via a lens 18, a light receiving end 14A of the fiber light guide 14 and a light guide end 14B of the fiber light guide 14 by selectively energizing the movable mirror 46. For diagnostic purposes, both halogen light and flashlight are required.

In the camera unit 3, optical images transferred from the fiber image guide 12 are received via a lens 22 and a lens 62 and thereafter focused on the solid-state image sensor (referred to as "image sensor") 60, a power supply source 64 is connected to the solid-state image sensor 60 so as to drive it, and an interface circuit 66 is connected between the image sensor 60 and the power supply source 64 so as to properly apply image signals derived from the image sensor 60 to the camera control unit 5.

The camera control unit 5 operates so that control signals e.g. a clock pulse signal are supplied to the image sensor 60 and also to the power supply source 64 so that those circuit elements are controlled to derive the necessary image signals. Further, according to the camera control unit 5, a synchronizing signal is superimposed to the image signal so that it is displayed on the monitor 6. The control signal is also applied to a flashlight control apparatus 50 for controlling the flashlight control operation which will be described later on.

In a normal condition, the movable mirror 46 is set to the halogen lamp side in the light source unit 3 so that the diseased portion (not shown) is illuminated by the halogen lamp 42 through the fiber light guide 14 in order to observe the diseased portion by the monitor 6. Therefore the image signal of the diseased portion of the patient (not shown) is derived from the image sensor 60 of the camera unit 2. This signal is properly processed by the known processing method in the camera control unit 5 so as to deliver it as a TV signal from the output terminal of the camera control unit, which is displayed on the monitor 6. Simultaneously, the photo-metric signal which is required for the present invention is independently derived from the camera control unit 5. In other words this photo-metric signal is derived from the image signal obtained from the image sensor 60 during monitor purposes only. Then the photo-metric signal is applied to the flashlight control apparatus 50. The flashlight control apparatus 50 utilizes this signal so as to obtain an adequate quantity of exposure for the flashlight photography. In this embodiment, an exposure time is calculated as the quantity of the exposure. The exposure time is used to control the flash tube 44.

A description of the control circuit for the flashlight exposure now follows.

As to controlling the flash tube and the solid-state image sensor, since there exists a proportional relation between the flashing time of the flash tube i.e., the quantity of flashlight given to the image sensor, and the brightness signal level of the flashlight and halogen lamp outputs, there are advantages according to the invention in that the above-described flashing time of the flash tube can be calculated in advance from the brightness signal lever of the halogen lamp 42. That is, the quantity of flashlight given to the image sensor "Fi" will be represented by the following equation, assuming that a ratio of the brightness output of the flash tube 44 to the maximum brightness output of the halogen lamp 4 is "A".

$$Fi = k \cdot (1/Ib \times A)$$

"Ib" is the brightness signal level of the image sensor during the diagnosis except the photographing operation (i.e., the photo-metric signal level), and "k" is a proportional constant. It should be noted that the brightness signal level of the image sensor during monitoring can be varied by adjusting a diaphragm or changing the power, or current supply to the halogen lamp.

Consequently if the flashlight of the flash tube 44 is controlled based upon the calculated value, the photographic signal of the foreground subject taken under an adequate exposure can be obtained from the image sensor 60. Generally speaking, the read-out time from the image sensor is 1/60 sec. (i.e., 1 TV frame=approx. 16 m sec.) while the time required for controlling the flashlight of the flash tube is at the most 1 m sec. Accordingly it is necessarily required to previously program the quantity of the flashlight given to the image sensor, and thus to control the exposure time of the flash tube based upon the programed value. In other words, due to the above-described timing relation, it is practically impossible to control the turn-off timing of the flash tube after receiving the flashlight reflection from the foreground subject.

The flashlight control apparatus or circuit 50 is comprised of a turn-on (ignition)/turn-off control circuit for the flash tube 80 and a programmed exposure/light processing circuit 90. The turn-on/turn-off control circuit 80 is per se known, in which a charging current from a charging circuit 81 which is connected to a power supply source (not shown) flows through a main capacitor 82, preparation of the flashlight is accomplished when the charging current becomes zero. Since the charging voltage across the main capacitor 82 is being applied to a thyristor 83 series-connected to the flash tube 44, the thyristor 83 is turned on when a trigger 84 is actuated, so that the flash tube 44 is ignited for photography. It should be noted that in this case, the movable mirror 46 is removed from over the flash tube 44 so as to interrupt the illumination of the halogen lamp. According to the invention, when a predetermined time has passed since the foreground subject (not shown) is illuminated by the flashlight through the fiber light guide 14, the flashing of the flash tube 44 is forcibly interrupted by the turn-on/turn-off control circuit 80.

Meanwhile the programmed exposure/light processing circuit 90 is constituted by a normal integration circuit 91, a pulse generating circuit 92, and a light processing circuit 93. Into this processing circuit 90, the photo-metric signal has been applied from the camera control unit 5 before the ignition of the flash tube 44. As a result, a desirable quantity of the flashlight to be given to the foreground subject, can be calculated in accordance with the above-mentioned equation in the processing circuit 93. Based upon the desirable quantity of the flashlight, an integration quantity is programmed in the integration circuit 91. The programmed value is changed into a corresponding duration time for the flashing. Accordingly when a predetermined integration level, i.e., a predetermined time has passed by counting of clock pulses from the pulse generator 92, a turn-off pulse is produced from the pulse generator 92, so that this turn-off pulse can turn-on another thyristor 85, which causes the flash tube 44 to be turnedoff immediately through commutation capacitor 86.

After completing a series of the flashlight control operation, the image signal taken by photographing the foreground subject under the flashlight is temporarily stored in a frame memory (not shown) and thereafter is derived as a still picture from the camera control unit 5.

When the photographing operation is accomplished, the movable mirror 46 is again set to the halogen lamp side, so that as the halogen lamp illuminates the foreground subject, an image signal for diagnosis purposes is derived from the image sensor 60. Thereafter this image signal is processed in the camera control unit 5 in the known method and displayed on the monitor 6.

Figure 4A:
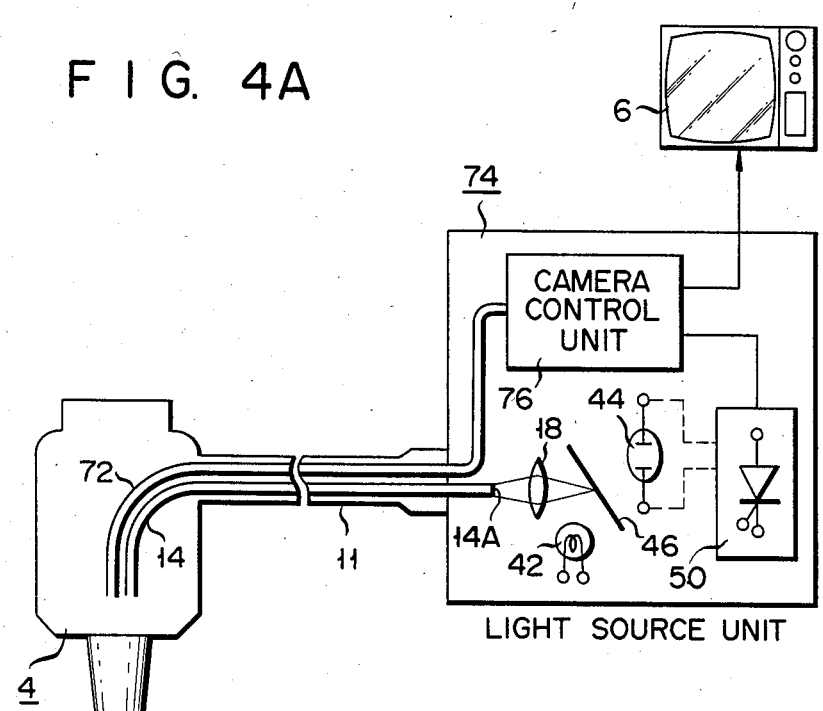
FIG. 4A is a schematic diagram of a flashlight control apparatus combined with an endoscope according to another preferred embodiment of the present invention.
Figure 4B:
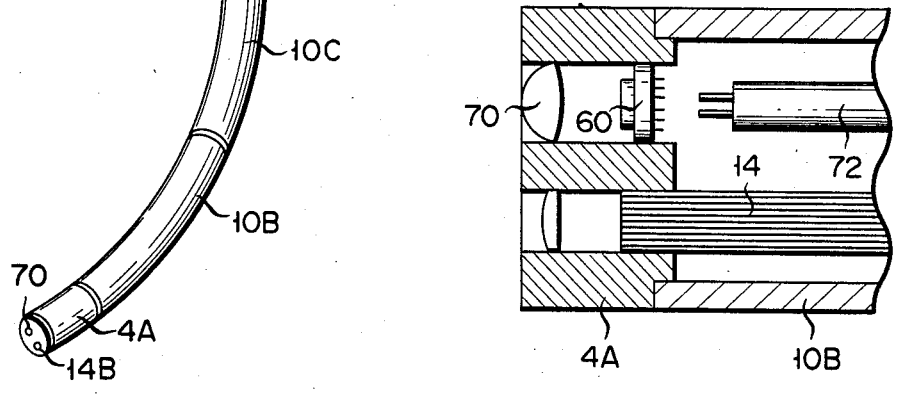
FIG. 4B is an enlarged cross-sectional view of the distal end of the endoscope shown in FIG. 4A.

Referring to FIGS. 4A and 4B, another preferred embodiment will be now explained. As easily seen from the foregoing embodiment shown in FIG. 2, the solid-state image sensor 60 is mounted in the camera unit 2. Alternatively in this embodiment, it can be mounted in the distal end 4A of the endoscope body 4 (see FIG. 4B). That is, the fiber image guide 12 is not employed in this embodiment, the image sensor 60 is fixed in the distal end 4A, and a focusing lens 70 is arranged in front of the light receiving face of the image sensor 60 so as to focus the optical image of the foreground subject (not shown). A supply of driving power for the image sensor and also a transfer of the image signal are performed by a transferring member e.g. a signal cable 72 which is connected to the camera control unit 76 in a light source unit 74. Another convex lens is arranged in the distal end 4A of the endoscope body 4 in opposite to the fiber light guide 14.

The driving power supply source and the interface circuit (neither shown) are also assembled in the camera control unit 76.

Figure 3:
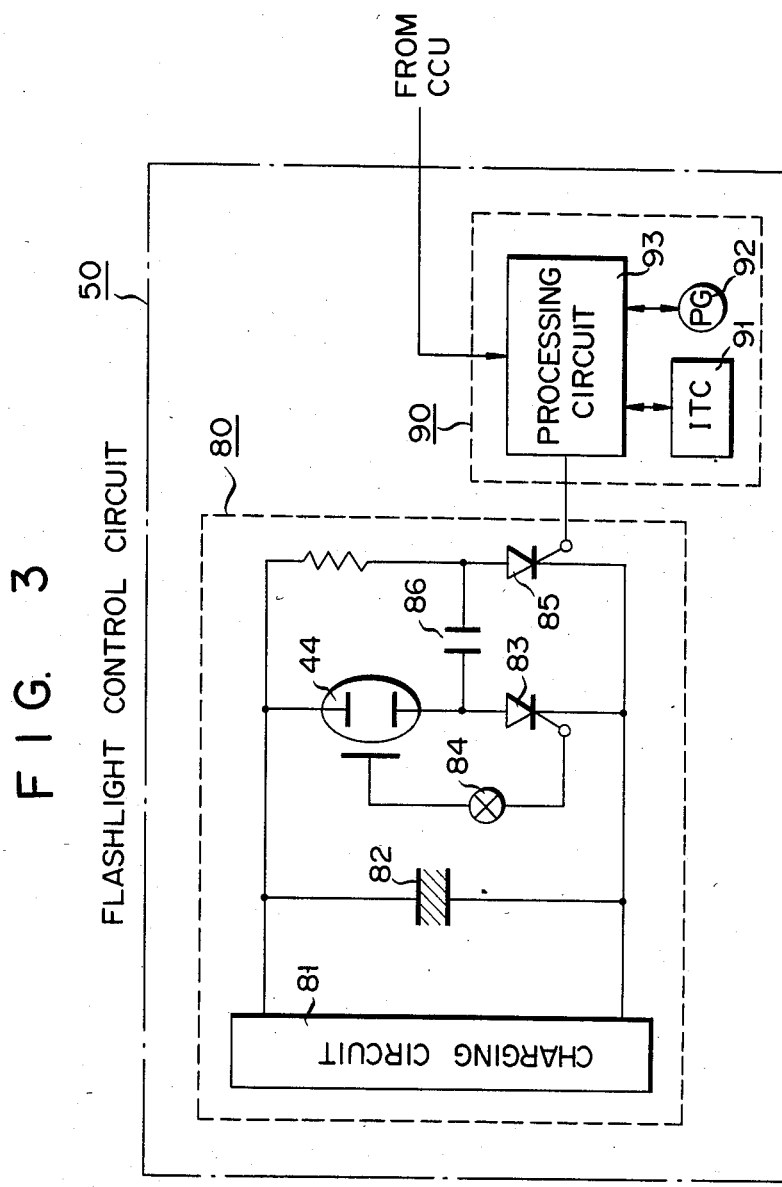
FIG. 3 is a detailed circuit diagram of the flashlight control apparatus shown in FIG. 2.

Since the operation of this embodiment is completely identical to that of the previous embodiment shown in FIGS. 2 and 3, the explanation thereof will be omitted.

In accordance with the present invention, when the illumination of an diseased portion which is observed by the endoscope is insufficient for photographing it, an adequate quantity of flashlight can be easily obtained by the flashlight control apparatus. High-speed photography can also be realized for such a disease portion e.g., a stomach by means of the flashlight control apparatus according to the invention. Other advantages are provided in that the output signal derived from the single image sensor can be utilized for not only the image monitoring, but also the measurement of the luminance of the foreground subject. Further advantages are provided in that since a photo-metric optical element can be omitted due to a common use of the image sensor, the camera unit can be made compact, and also the alignment of the optical system can be avoided.

While the invention has been described in terms of certain preferred embodiments, and exemplified with respect thereto, those skilled in the art will readily appreciate that various modifications, changes, omissions and substitutions may be made without departing from the spirit of the invention.

In the previous embodiments the photo-metric signal was obtained by scanning the entire light receiving face of the image sensor, but it is possible to scan a part of the light receiving face thereof. The latter photo-metric signal is suitable for photographing such a diseased portion that has many concave-convex parts.

Other known circuit arrangements may be substituted for the turn-on/turn-off control circuit 80 and the programmed exposure/light processing circuit 90.

The signal cable 72 can be substituted by an optical fiber which may transfer a light-modulated image signal from the image sensor via a signal to light modulator.

The halogen lamp may be alternatively provided in the distal end of the endoscope body to which a power voltage is applied.

Another modification may be realized. That is, the flash tube (i.e., long-arc xenon lamp) may be substituted by a short-arc xenon lamp. This short-arc xenon lamp is turned off in such a manner that an electronic shutter is controlled by the programmed exposure time so as to turn on a thyristor which is connected in parallel to the short-arc xenon lamp, so that a voltage being applied across the xenon lamp is short-circuited by means of the thyristor. A detailed description thereof is disclosed in Japanese Pat. No. 855418 (1976).

What is claimed is:

1. A light flash control apparatus for an endoscope having an image guide member and a light guide member, comprising:

light source means, coupled to one end of the light guide member, including at least a lamp for illuminating an object during monitoring, a flash tube for illuminating the object during photographing, and a light path selecting member for selectively transferring light from one of said lamp and said flash tube through one end of the light guide member to an object under examination when located near the other end of the light guide member;

camera means, adapted to be detachably mounted to said endoscope, including a solid-state image sensor optically coupled to the image guide member, for producing at least image signals of the object as photometric signals when the object is illuminated by said lamp;

camera control means connected to receive the photometric signals from the solid-state sensor of the camera means; and light flash control means, coupled to said camera control means and to said flash tube, including a turn-on/turn-off control circuit and an exposure/light processing circuit, said exposure/light processing circuit processing the photometric signals so as to precalculate an exposure value desirable for photographing, and said turn-on/turn-off control circuit controlling both the turning on and off of said flash lamp based upon said precalculated exposure value during a photographing operation.

2. A flashlight control apparatus as claimed in claim 1, wherein said turn-on/turn-off control circuit includes a charging circuit having a charging capacitor, a turn-on thyristor which is series-connected to said flash tube and the trigger gate of which is connected to trigger means, and a turn-off thyristor which is connected parallel to said turn-on thyristor via a commutation capacitor; and said exposure/light processing circut includes a pulse generator for generating a clock pulse signal, an integration circuit, and a processing circuit which is connected to the trigger gate of said turn-off thyristor and also to said camera control means so as to receive said photo-metric signal therefrom, wherein said processing circuit derives said exposure value from said photo-metric signal so that said exposure value is calculated by utilizing brightness signal levels of said photo-metric signal and stored as an exposure time for said flash tube in said integration circuit, and control the turn-off of said flash tube so that a turn-off signal is applied to said trigger gate of the turn-off thyristor when the number of said clock pulse reaches said exposure time for the flash tube.

3. A light flash control apparatus for an endoscope having a light guide member, comprising:

light source means, coupled to one end of the light guide member, including at least a lamp for illuminating an object during monitoring, a flash tube for illuminating the object during photographing, and a light path selecting member for selectively transferring light from one of said lamp and said flash tube through one end of the light guide member to an object under examination when located near the other end of the light guide member;

camera means, adapted to be mounted to a distal end of the endoscope, including a solid-state image sensor and signal cable means one end of which is coupled to said image sensor at said distal end, for producing at least image signals of the object as photometric signals when the object is illuminated by said lamp;

camera control means coupled to the other end of said signal cable means to receive the photometric signals from the solid-state image sensor of the camera means; and light flash control means, coupled to said camera control means and to said flash tube, including a turn-on/turn-off control circuit and an exposure/light processing circuit, said exposure/light processing circuit processing the photometric signals so as to precalculate an exposure value desirable for photographing, and said turn-on/turn-off control circuit controlling both the turning on and off of said flash lamp based upon said precalculated exposure value during a photographing operation.

4. A flashlight control apparatus as claimed in claim 3, wherein said turn-on/turn-off control circuit includes a charging circuit having a charging capacitor, a turn-on thyristor which is series-connected to said flash tube and the trigger gate of which is connected to trigger means, and a turn-off thyristor which is connected parallel to said turn-on thyristor via a commutation capacitor; and said exposure/light processing circuit includes a pulse generator for generating a clock pulse signal, an integration circuit, and a processing circuit which is connected to the trigger gate of said turn-off thyristor and also to said camera control means so as to receive said photo-metric signal therefrom, wherein said processing circuit derives said exposure value from said photo-metric signal so that said exposure value is calculated by utilizing brightness signal levels of said photo-metric signal and stored as an exposure time for said flash tube in said integration circuit, and controls the turn-off of said flash tube that a turn-off signal is applied to said trigger gate of the turn-off thyristor when the number of said clock pulse reaches said exposure time for the flash tube.

* * * * *

UNITED STATES PATENT AND TRADEMARK OFFICE
CERTIFICATE OF CORRECTION

PATENT NO. : 4,561,429

DATED : December 31, 1985

INVENTOR(S) : Ken Sato et al

It is certified that error appears in the above-identified patent and that said Letters Patent is hereby corrected as shown below:

COLUMN 6, line 64, change "body 4 in" to --body 4, --.

COLUMN 8 (claim 2), line 35, change "control" to

--controls--;

COLUMN 10 (claim 4), line 10, after "flash tube"

insert --so--.

Signed and Sealed this

Twentieth Day of May 1986

[SEAL]

Attest:

DONALD J. QUIGG

Attesting Officer

Commissioner of Patents and Trademarks